US012766027B2

(12) United States Patent
Carlsson et al.

(10) Patent No.: US 12,766,027 B2
(45) Date of Patent: Oct. 20, 2026

(54) SYSTEM AND METHOD FOR OSTOMY INFORMATION COLLECTION AND ANALYSIS

(71) Applicant: Hollister Incorporated, Libertyville, IL (US)

(72) Inventors: Jonas P. Carlsson, Chicago, IL (US); Ryan S. Park, Northbrook, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 859 days.

(21) Appl. No.: 18/015,244

(22) PCT Filed: Jul. 27, 2021

(86) PCT No.: PCT/US2021/070961
§ 371 (c)(1),
(2) Date: Jan. 9, 2023

(87) PCT Pub. No.: WO2022/026995
PCT Pub. Date: Feb. 3, 2022

(65) Prior Publication Data

US 2023/0255811 A1 Aug. 17, 2023

Related U.S. Application Data

(60) Provisional application No. 63/058,214, filed on Jul. 29, 2020.

(51) Int. Cl.
*A61F 5/445* (2006.01)
*A61F 5/44* (2006.01)
(Continued)

(52) U.S. Cl.
CPC ............ *A61F 5/4404* (2013.01); *A61F 5/445* (2013.01); *G01M 3/16* (2013.01); *G16H 40/67* (2018.01)

(58) Field of Classification Search
CPC ....... A61F 5/4404; A61F 5/445; G16H 40/67; G01M 3/16
See application file for complete search history.

(56) References Cited

U.S. PATENT DOCUMENTS 9,928,341 B2 3/2018 Angelides
10,199,126 B2 2/2019 Angelides
(Continued)

FOREIGN PATENT DOCUMENTS

WO 2018/218310 A1 12/2018
WO 2019/040908 A1 2/2019
(Continued)

OTHER PUBLICATIONS

Extended European Search Report issued in connection with EP application No. 24154103.6 dated Jul. 4, 2024, 10 pages.
(Continued)

*Primary Examiner* — Guy K Townsend
(74) *Attorney, Agent, or Firm* — Klintworth & Rozenblat LLP

(57) ABSTRACT

An ostomy leak detection system (10) includes a sensor device (20) configured to detect one or more parameters or parameter values indicative of a condition of an ostomy product, and one or more auxiliary devices (30) operably connected to the sensor device and configured to receive sensor information indicative of the condition of the ostomy product from the sensor device. The one or more auxiliary devices includes at least one of monitoring device (32), a wearable device (34), a consumer electronic device (36) and a server device (38). A method for ostomy leak detection system analysis includes receiving ostomy system information relating to an ostomy product. The ostomy system information may be information relating to factors affecting performance of the ostomy product. The method further
(Continued)

includes determining characteristic information based on the ostomy system information.

12 Claims, 4 Drawing Sheets

(51) Int. Cl.
*G01M 3/16* (2006.01)
*G16H 40/67* (2018.01)

(56) References Cited

U.S. PATENT DOCUMENTS

| | | | | |
|---|---|---|---|---|
| 10,504,020 | B2 | 12/2019 | Trenholm et al. | |
| 11,534,323 | B2 * | 12/2022 | Hansen | G16H 30/40 |
| 2010/0030167 | A1 * | 2/2010 | Thirstrup | A61B 5/746 340/657 |
| 2019/0013381 | A1 | 1/2019 | Liou et al. | |
| 2019/0133811 | A1 * | 5/2019 | Seres | A61B 5/002 |
| 2019/0133812 | A1 * | 5/2019 | Seres | A61B 5/002 |
| 2019/0142623 | A1 | 5/2019 | Norman et al. | |
| 2019/0240059 | A1 * | 8/2019 | Seres | A61F 5/4404 |
| 2020/0000624 | A1 * | 1/2020 | Gibbons | A61B 5/444 |
| 2020/0246174 | A1 * | 8/2020 | Hansen | A61F 5/443 |
| 2020/0246175 | A1 | 8/2020 | Ask et al. | |
| 2020/0246176 | A1 * | 8/2020 | Hansen | A61F 5/445 |
| 2020/0246177 | A1 | 8/2020 | Ask et al. | |
| 2020/0375784 | A1 * | 12/2020 | Hansen | A61F 5/443 |
| 2020/0375785 | A1 * | 12/2020 | Hansen | A61B 90/361 |
| 2020/0390587 | A1 * | 12/2020 | Svanegaard | G16H 40/40 |
| 2020/0395120 | A1 * | 12/2020 | Svanegaard | A61F 5/4404 |
| 2020/0405230 | A1 * | 12/2020 | Svanegaard | A61B 5/6813 |
| 2021/0000414 | A1 * | 1/2021 | Svanegaard | A61B 5/0002 |
| 2021/0007663 | A1 * | 1/2021 | Svanegaard | A61B 5/4851 |
| 2021/0007881 | A1 * | 1/2021 | Svanegaard | A61F 5/4404 |
| 2021/0059603 | A1 * | 3/2021 | Svanegaard | A61B 5/4851 |
| 2021/0275341 | A1 | 9/2021 | Kristoffer | |
| 2021/0353448 | A1 | 11/2021 | George et al. | |
| 2021/0369491 | A1 | 12/2021 | Holden | |
| 2022/0117771 | A1 | 4/2022 | Fearn et al. | |
| 2022/0257405 | A1 | 8/2022 | Peder et al. | |
| 2022/0265457 | A1 * | 8/2022 | Emborg | A61F 5/448 |
| 2022/0313473 | A1 * | 10/2022 | Schertiger | A61F 5/4404 |
| 2022/0378602 | A1 * | 12/2022 | Hansen | A61F 5/4404 |
| 2023/0031979 | A1 * | 2/2023 | Windeballe | A61F 5/4404 |

FOREIGN PATENT DOCUMENTS

| | | | | |
|---|---|---|---|---|
| WO | 2019/094635 | A1 | 5/2019 | |
| WO | 2019/120424 | A1 | 6/2019 | |
| WO | 2019/120425 | A1 | 6/2019 | |
| WO | 2019/120426 | A1 | 6/2019 | |
| WO | 2019/120427 | A1 | 6/2019 | |
| WO | 2019/120428 | A1 | 6/2019 | |
| WO | 2019/120429 | A1 | 6/2019 | |
| WO | 2019/120430 | A1 | 6/2019 | |
| WO | 2019/120432 | A1 | 6/2019 | |
| WO | 2019/120433 | A1 | 6/2019 | |
| WO | 2019/120434 | A1 | 6/2019 | |
| WO | 2019/120435 | A1 | 6/2019 | |
| WO | 2019/120436 | A1 | 6/2019 | |
| WO | 2019/120437 | A1 | 6/2019 | |
| WO | 2019/120440 | A1 | 6/2019 | |
| WO | 2019/120441 | A1 | 6/2019 | |
| WO | 2019/120442 | A1 | 6/2019 | |
| WO | 2019/120443 | A1 | 6/2019 | |
| WO | 2019/120444 | A1 | 6/2019 | |
| WO | 2019/120445 | A1 | 6/2019 | |
| WO | 2019/120448 | A1 | 6/2019 | |
| WO | 2019/120449 | A1 | 6/2019 | |
| WO | 2019/120450 | A1 | 6/2019 | |
| WO | 2019/120451 | A1 | 6/2019 | |
| WO | 2019/120452 | A1 | 6/2019 | |
| WO | 2019/120453 | A1 | 6/2019 | |
| WO | WO-2019120446 | A1 * | 6/2019 | A61F 5/443 |
| WO | WO-2019120458 | A1 * | 6/2019 | A61F 5/445 |
| WO | 2019/149330 | A1 | 8/2019 | |
| WO | 2019/161859 | A1 | 8/2019 | |
| WO | 2019/161860 | A1 | 8/2019 | |
| WO | 2019/161861 | A1 | 8/2019 | |
| WO | 2019/161862 | A1 | 8/2019 | |
| WO | 2019/161863 | A1 | 8/2019 | |
| WO | 2019/169327 | A1 | 9/2019 | |
| WO | 2019/174687 | A1 | 9/2019 | |
| WO | 2019/174692 | A1 | 9/2019 | |
| WO | 2019/174693 | A1 | 9/2019 | |
| WO | 2019/174694 | A1 | 9/2019 | |
| WO | 2019/174695 | A1 | 9/2019 | |
| WO | 2019/174696 | A1 | 9/2019 | |
| WO | 2019/174697 | A1 | 9/2019 | |
| WO | 2019/174698 | A1 | 9/2019 | |
| WO | 2019/174699 | A1 | 9/2019 | |
| WO | 2019/238180 | A1 | 12/2019 | |
| WO | 2019/238181 | A1 | 12/2019 | |
| WO | 2019/238182 | A1 | 12/2019 | |
| WO | 2019/238183 | A1 | 12/2019 | |
| WO | 2020/035121 | A1 | 2/2020 | |
| WO | 2020/076605 | A1 | 4/2020 | |
| WO | 2020/076607 | A1 | 4/2020 | |
| WO | 2020/076609 | A1 | 4/2020 | |
| WO | 2020/123771 | A2 | 6/2020 | |
| WO | WO2020125906 | A1 | 6/2020 | |
| WO | WO2020125907 | A1 | 6/2020 | |
| WO | 2020/156624 | A1 | 8/2020 | |
| WO | 2020/156625 | A1 | 8/2020 | |
| WO | 2020/156626 | A1 | 8/2020 | |
| WO | 2020/169162 | A1 | 8/2020 | |
| WO | 2020/173534 | A1 | 9/2020 | |
| WO | 2020/216426 | A1 | 10/2020 | |
| WO | 2020/216427 | A1 | 10/2020 | |
| WO | 2020/216429 | A1 | 10/2020 | |
| WO | 2020/259775 | A1 | 12/2020 | |
| WO | 2021/063463 | A1 | 4/2021 | |
| WO | 2021/063466 | A1 | 4/2021 | |
| WO | 2021/165703 | A1 | 8/2021 | |
| WO | 2021/165705 | A1 | 8/2021 | |
| WO | 2021/185425 | A1 | 9/2021 | |
| WO | 2021/209104 | A1 | 10/2021 | |
| WO | 2022/063379 | A1 | 3/2022 | |
| WO | 2022/078561 | A1 | 4/2022 | |
| WO | 2022/207049 | A1 | 10/2022 | |

OTHER PUBLICATIONS

Extended European Search Report issued in connection with EP application No. 25182832.3 dated Oct. 24, 2025, 07 pages.
"Server." Merriam-Webster.com Dictionary, Merriam-Webster, https://www.merriam-webster.com/dictionary/server. Accessed Jan. 8, 2025, 04 pages.
Wikipedia: "Server (computing)", Wikipedia, accessed Jul. 15, 2020, in 09 pages, XP093253548 URL: https://en.wikipedia.org/w/index.php?title=Server(computing)&oldid=967791154.
International Search Report issued Nov. 9, 2021 by ISA/EPO in connection with PCT/US2021/070961.
Written Opinion issued Nov. 9, 2021 by ISA/EPO in connection with PCT/US2021/070961.
International Preliminary Report on Patentability issued Feb. 9, 2023 by WIPO in connection with PCT/US2021/070961.
Australian Office Action issued in connection with AU application No. 2021315929 dated May 7, 2026, 04 pages.

* cited by examiner

SYSTEM AND METHOD FOR OSTOMY INFORMATION COLLECTION AND ANALYSIS

This is a National Stage Application of International Patent Application No. PCT/US2021/070961 filed Jul. 27, 2021, which claims the benefit of and priority to U.S. Provisional Application No. 63/058,214 filed Jul. 29, 2020, the entirety of which are incorporated fully herein by reference.

BACKGROUND

The following description relates generally to an ostomy leakage detection system, and in particular, to a system and method for ostomy information collection and analysis.

An ostomy pouch system typically includes a pouch formed from opposing sidewalls defining an internal collection area, an inlet opening for receiving a stoma, and an ostomy appliance for attaching the pouch to a user. The ostomy appliance may include, for example, an ostomy barrier of a one-piece pouch system, which is attached to one of the pouch sidewalls proximate an inlet opening, a faceplate for a two-piece pouch system configured to releasably engage a pouch, and a barrier ring. The ostomy appliance may include a skin barrier material for adhering to and sealing against user's peristomal skin surrounding the stoma.

The ostomy appliance may be susceptible to ostomy effluent leakage, and the seal formed between the skin barrier material and the user may weaken. Often times, the user may be unaware of or cannot easily assess an extent of weakening in the seal. Thus, the user may not become aware of a weakened seal, and consequently, the ostomy effluent may leak through to an exterior of the ostomy appliance.

Accordingly, it is desirable to provide a leakage detection system for ostomy products and a system and method for ostomy information collection and analysis.

SUMMARY

In one aspect, an ostomy leak detection system includes a sensor device configured to detect one or more parameters or parameter values indicative of a condition of an ostomy product, and one or more auxiliary devices operably connected to the sensor device and configured to receive sensor information indicative of the condition of the ostomy product from the sensor device. The one or more auxiliary devices includes at least one of monitoring device, a wearable device, a consumer electronic device and a server device.

In an embodiment, the ostomy leak detection system may be configured to detect, determine and/or receive ostomy system information and store the ostomy system information. In an embodiment, the ostomy leak detection system may determine characteristic information based at least in part on the ostomy system information. In an embodiment, the ostomy leak detection system may aggregate and store ostomy system information and/or characteristic information from a plurality of users and/or ostomy products.

In an embodiment, the sensor device may be a leakage sensor device configured to detect electrical resistance. In an embodiment, the one or more auxiliary devices may include the wearable device operably connected to the sensor device and a consumer electronic device communicably connected to the wearable device via a wireless connection. In an embodiment, the one or more auxiliary devices may include a monitoring device operably coupled to the sensor device, a wearable device communicably coupled to the monitoring device, and a consumer electronic device communicably connected to the wearable device via a wireless connection.

In an embodiment, the at least one auxiliary device may include a server device communicably coupled to one or more of the wearable device and the consumer electronic device. In an embodiment, the ostomy leak detection system may further include an ostomy product. The sensor device may be operably connected to the ostomy product.

In another aspect, a method for ostomy leak detection system analysis includes receiving ostomy system information relating to an ostomy product. The ostomy system information may be information relating to factors affecting performance of the ostomy product. The method also includes determining characteristic information based on the ostomy system information.

In an embodiment, the method may further include providing a notification based on the characteristic information. In an embodiment, receiving ostomy system information may further include aggregating ostomy system information from multiple ostomy leak detection systems. In an embodiment, the characteristic information may include at least one of product consumption information, leak information, inventory information, stoma health information, replacement information, recommendation information and predictive information.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
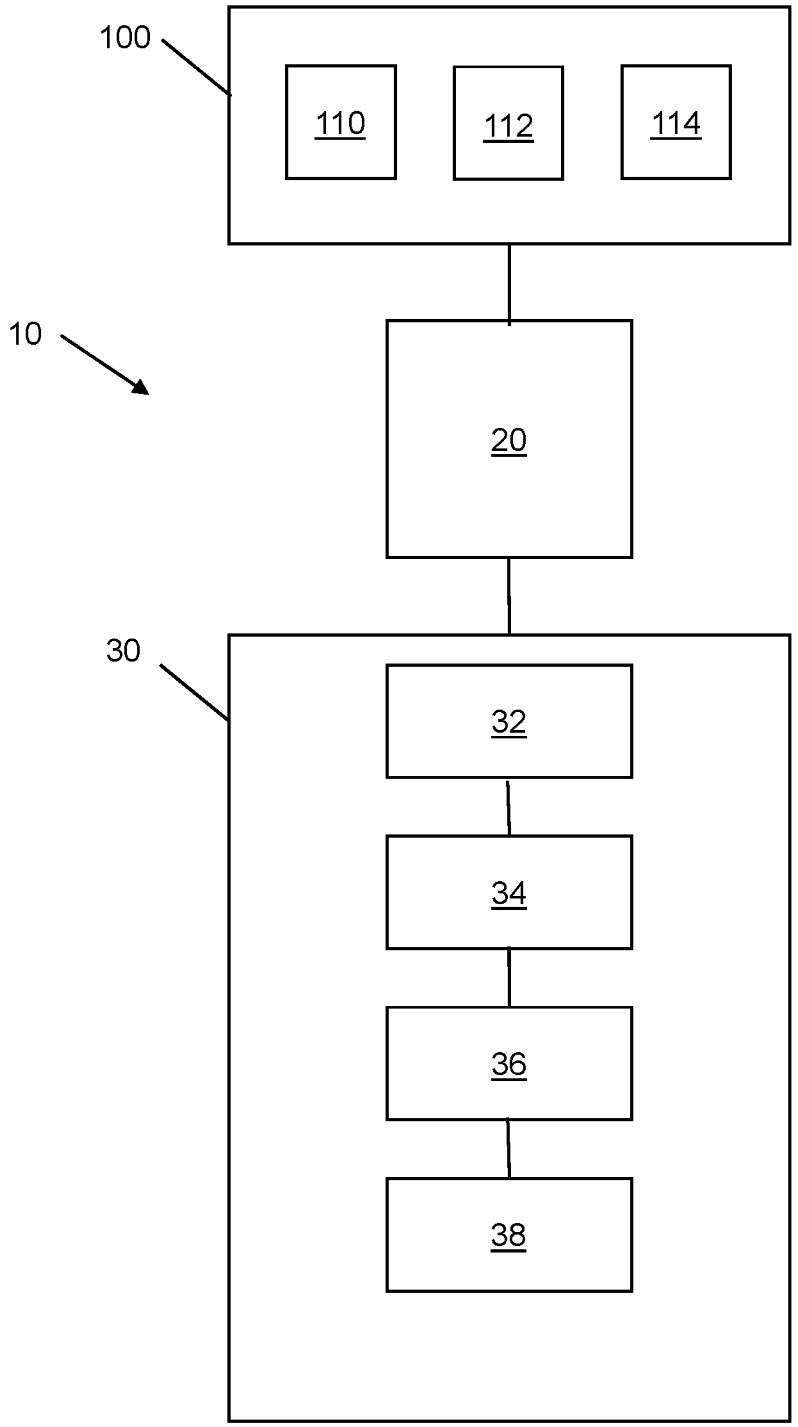
FIG. 1 is a block diagram schematically illustrating an example of an ostomy leak detection system according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

According to embodiments, an ostomy leak detection system may generally include a sensor device and one or more auxiliary devices. The sensor device may be used with an ostomy product, such as an ostomy appliance, ostomy pouch or ostomy accessory. The ostomy appliance may be, for example, an ostomy barrier or faceplate. The ostomy pouch may be coupled to the ostomy appliance. The ostomy appliance may be adhered to a user's body to seal around a stoma and the ostomy pouch may receive effluent discharged from the stoma. In an embodiment, the ostomy accessory may be attached to a body side of the ostomy appliance and thus, may be disposed between the user and the ostomy appliance when secured to the user. In an embodiment, the ostomy leak detection system may include one or more ostomy products.

The ostomy leak detection system may be configured to receive information from one or more sources, such as, but not limited to, a sensor device, an auxiliary device and/or user input. The ostomy leak detection system may also determine information, for example, based on the received information. In an embodiment, the received information may be ostomy system information. Ostomy system information may be information associated with various factors which may affect performance of an ostomy product. Information determined by the ostomy leak detection system based at least in part on the ostomy system information may be referred to generally herein as characteristic information. Characteristic information may refer to information relating performance characteristics of an ostomy product.

In an embodiment, the sensor device may be configured to provide sensor information to one or more auxiliary devices. For example, the sensor device may be configured to detect one or more parameters or parameter values which may be indicative of a condition or performance characteristic of an ostomy product. Such parameters may include, for example, electrical resistance, impedance, color, temperature, strain, light and the like. In an embodiment, the sensor device may be a leakage sensor configured to provide sensor information for determining whether effluent is leaking radially outward from a stoma opening. For example, the sensor device may detect values of one or more parameters which may be indicative of a leak, such as, but not limited to, electrical resistance. The sensor device may detect the one or more parameters at a surface of or within the ostomy appliance or ostomy accessory. In an embodiment, the sensor device may be at least partially disposed on a body side of the ostomy appliance or ostomy accessory and may be configured to detect the one or more parameters at the user's skin surface.

The one or more auxiliary devices may include, for example, a monitoring device, a wearable device, a consumer electronic device, and/or a server device. One or more of the auxiliary devices may include a processor, a memory and a communication device. The processor may be, for example, a microprocessor or other suitable computer processor or processor-like device. The processor may be configured to execute program instructions and perform operations based on the executed program instructions. For example, the processor may control operations of other devices or components based on the executed program instructions. The memory may be a non-transitory computer-readable storage medium configured to store the program instructions. The memory may also store other information, such as the sensor information provided by the sensor device. Sensor information may include, for example, parameter information and/or parameter value information. The communication device may be a transceiver or transceiver-like device. The communication device may be configured to transmit and/or receive information via a wired and/or wireless communication interface.

One or more of the auxiliary devices may also include a user interface device. The user interface device may be configured to receive input information from a user and/or may be configured to output information to a user. The user interface device may include, for example, one or more of a keyboard, key pad, pointer, button, switch, knob, lever, dial, touchscreen display, microphone, speaker, haptic motor, lights or LEDs, biometric sensor, optical sensor and/or combinations thereof. Other known, suitable user interfaces are envisioned as well.

In some embodiments, the sensor device may be integrated or combined with one more of the auxiliary devices and may include one or more of the components of the auxiliary devices described above. For example, in an embodiment, the sensor device and the monitoring device may be provided together as a unit.

In an embodiment, the sensor device and the monitoring device may be provided at the ostomy appliance. The monitoring device may receive the sensor information from the sensor device. The wearable device may be removably coupled to monitoring device and the ostomy appliance. The wearable device may be communicably connected to the monitoring device to receive information, such as the sensor information, from the monitoring device. In an embodiment, the wearable device may be communicably connected via a wireless connection to, for example, a consumer electronic device, such as a smart phone, tablet computer, laptop computer, desktop computer and the like. The consumer electronic device may receive information from the wearable device, such as the sensor information. The consumer electronic device may also transmit information to the wearable device. The consumer electronic device may be communicably connected to a server device, for example, over a communication network such as the Internet and/or a cellular network, and may transmit information to, and/or receive information from, the server device. In other embodiments, the wearable device may be communicably connected to the consumer electronic device via a wired connection and may transmit and/or receive information via the wired connection.

In other embodiments, the monitoring device may be communicably connected to the wearable device via a wireless connection. In still other embodiments, the monitoring device may be omitted, or integrated with the wearable device, and the wearable device may be connected directly to the sensor device and may receive information, such as sensor information, from the sensor device.

In some embodiments, the sensor device may be synced or baselined with one or more of the auxiliary devices to facilitate communication between the sensor device and the one or more auxiliary devices. The sensor device may be synced or baselined each time an ostomy product, such as an ostomy appliance, ostomy accessory or ostomy pouch is changed out or replaced. Accordingly, the auxiliary device may count a number of syncing operations and save the count as product consumption information. The syncing or baselining operation may be product specific. Accordingly, product consumption may be tracked based on the stored product consumption information. Use information may be tracked and stored as well. Use information may include, for example, length of use of an ostomy product. The use information may be derived from the product consumption information, for example, based on a length of time between syncing/baselining operations for a particular ostomy product.

An auxiliary device of the ostomy leak detection system may also determine inventory information for an ostomy product. The inventory information may be based at least in part on the product consumption information. In addition, SKU information of an ostomy product may be received by an auxiliary device. The SKU information may include, for example, quantity information of the ostomy product. The auxiliary device may further determine inventory information based on the quantity information.

The ostomy leak detection system, for example, by an auxiliary device, may provide a notification regarding the inventory information. For example, the notification may alert a user to a number of remaining ostomy products in a given supply. In an embodiment, the notification may be provided when the number of remaining ostomy products falls below a threshold value. In addition, the ostomy leak detection system, for example at an auxiliary device, may provide a prompt to a user to re-order an ostomy product based on the inventory information. The auxiliary device may be communicably connected to an ostomy product supplier and may re-order the ostomy product based on the inventory information.

In an embodiment, the ostomy leak detection system may be configured to detect, determine, or receive additional information. Additional information may be received, for example, via user input, sensors or other devices. The additional information may include, for example, leak information, gas information, and/or diet information. The additional information may be stored at one or more of the auxiliary devices.

In an embodiment, the ostomy leak detection system may be configured to detect, determine and/or receive stoma health information (including skin health information). In an embodiment, images of the stoma and/or peristomal skin may be captured by an image capture device. The images may be photographs, thermal images, or other suitable images. The images may be captured as a function of time. The images may be stored, for example, in the memory of an auxiliary device. The image capture device may be, for example, a camera, and may be integrated with or connected to an auxiliary device, such as a smart phone camera. The stoma health information may be determined based on an image or series of images which may show a change in appearance over time. In an embodiment, images of the stoma and/or peristomal area may be taken before application of an ostomy appliance to the user and upon removal of the ostomy appliance from the user.

In an embodiment, the ostomy leak detection system may be configured to contact an ostomy specialist, such as a WOC/ET nurse. Other ostomy specialists including technical support personnel, customer service personnel and the like may be contacted as well. In an embodiment, information, including images, stoma health information or other relevant information, stored in the ostomy leak detection system may be shared with or accessed by the ostomy specialist. In an embodiment, the ostomy specialist may be contacted via a consumer electronic device, such as a smart phone, tablet computer, laptop computer, desktop computer or other device configured for communication over a communication network. The ostomy specialist may be able to provide information to the user via the ostomy leak detection system, such as troubleshooting information or additional stoma health information including diagnostic information.

The stoma health information, including skin health information, may indicate a change in stoma health over time. Thus, the stoma health information may be beneficial from a clinical and/or health economic perspective.

The ostomy leak detection system, for example, by an auxiliary device, may be configured to detect, determine and/or receive wear time information for an ostomy product. In an embodiment, wear time information may be determined by aggregating information which may be relevant to product wear time from multiple users and analyzing the aggregated information. The aggregated information may include, for example, user country information, ostomy type information, and product type information, including long versus short wear information. The aggregated wear time information may be analyzed to determine, for example, average or median wear time for different products, in different locations, and for different ostomy types. Additional wear time information may be aggregated as well, including, but not limited to user age information, climate information, user activity information, product age information, product manufacture information, product source information and the like.

The aggregated wear time information may be useful for market access reasons, for example, to change utilization rates, change reimbursement rates, change standard practice in terms of recommended wear time per ostomy product.

In an embodiment, the ostomy leak detection system, for example, by an auxiliary device, may be configured to determine predictive information based on determined, detected and/or received information. In an embodiment, the predictive information may further be based on an artificial intelligence or machine learning training model and training data. In this manner, the ostomy leak detection system may track leaks and understand trends to determine predictive information for approximating future leak patterns and trends for particular products, user or both. The ostomy leak detection system may provide such information to a user, ostomy specialists, ostomy suppliers, ostomy manufacturers and the like.

In an embodiment, the predictive information may be based, at least in part, on sensor information provided by the sensor device. The sensor information may be, for example, information indicative of an effluent leak, an extent of effluent, and/or a location of an effluent leak. The predictive information may be based on other information as well, such as product information (e.g., type, model, etc.), ostomy type information, environmental information, activity information, wear time information, and/or other information relevant for predicting performance of an ostomy product. Aggregated data may be used as well.

By learning a patient and their leakage trends, the ostomy leak detection system may be able to predict when the ostomy product worn by the patient may be expected to leak and may alert the patient to change the ostomy product according to the predictive information. This may also be useful for providing product recommendations, e.g., to use a convex ostomy product. For example, if over 1 year, the patient typically experiences leakage at 9 o'clock after 2 days of use, the predictive information may be determined and could be used along with a clinician consult/recommendation to change the product they are using.

Different end users (i.e., patients) may have different types of stomas, outputs, body types, ages and the like. Accordingly, ostomy leak detection systems may store different user information depending on the end user, including but not limited to stoma type information, output information, body type information, age information and the like.

In an embodiment, the user information from different users may be aggregated. Similar attributes or information across the different users may be identified and used to provide, for example, product recommendations for the clinician and/or end user and may be able to influence which product(s) end user should use in certain timelines, for example, a first ostomy product may be recommended for a particular user post operation, a second product after 6 months, and a third product after 1 year. The present description is not limited to these examples however, and it is appreciated that a different number of products and different timelines may be recommended.

In addition, clinicians may limit inventory based on the predictive information by stocking products which are recommended for use for particular patients based on the predictive information. It is also envisioned that information detected, determined and/or received by the ostomy leak detection system may be used by an ostomy manufacturer or designer to design new ostomy products.

FIG. 1 is a block diagram schematically illustrating an example of an ostomy leak detection system 10 according to embodiments. The ostomy leak detection system 10 may include, for example, a sensor device 20 and one or more auxiliary devices 30. The one or more auxiliary devices 30 may include, for example, a monitoring device 32, a wearable device 34, a consumer electronic device 36 and/or a server device 38. In an embodiment, the ostomy leak detection system 10 may include or be coupled with one or more ostomy products 100, such as an ostomy appliance 110, an ostomy accessory 112 and/or an ostomy pouch 114.

Figure 2:
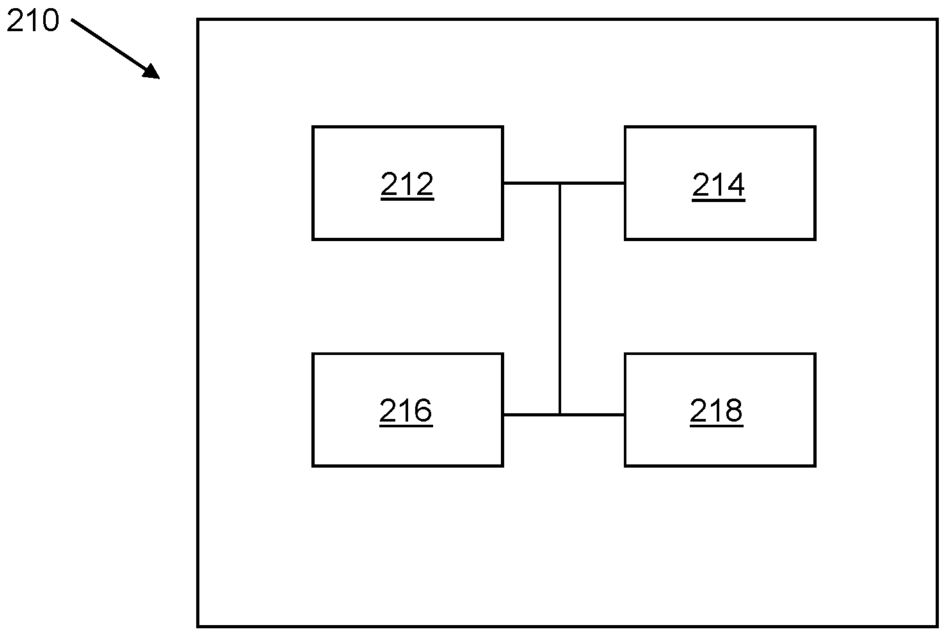
FIG. 2 is a block diagram schematically illustrating an example of an auxiliary device according to an embodiment.

FIG. 2 is a block diagram schematically illustrating an example of an auxiliary device 210 according to an embodiment. The auxiliary device 210 may include, for example, a processor 212, a memory 214, a communication device 216, and a user interface device 218.

Figure 3:
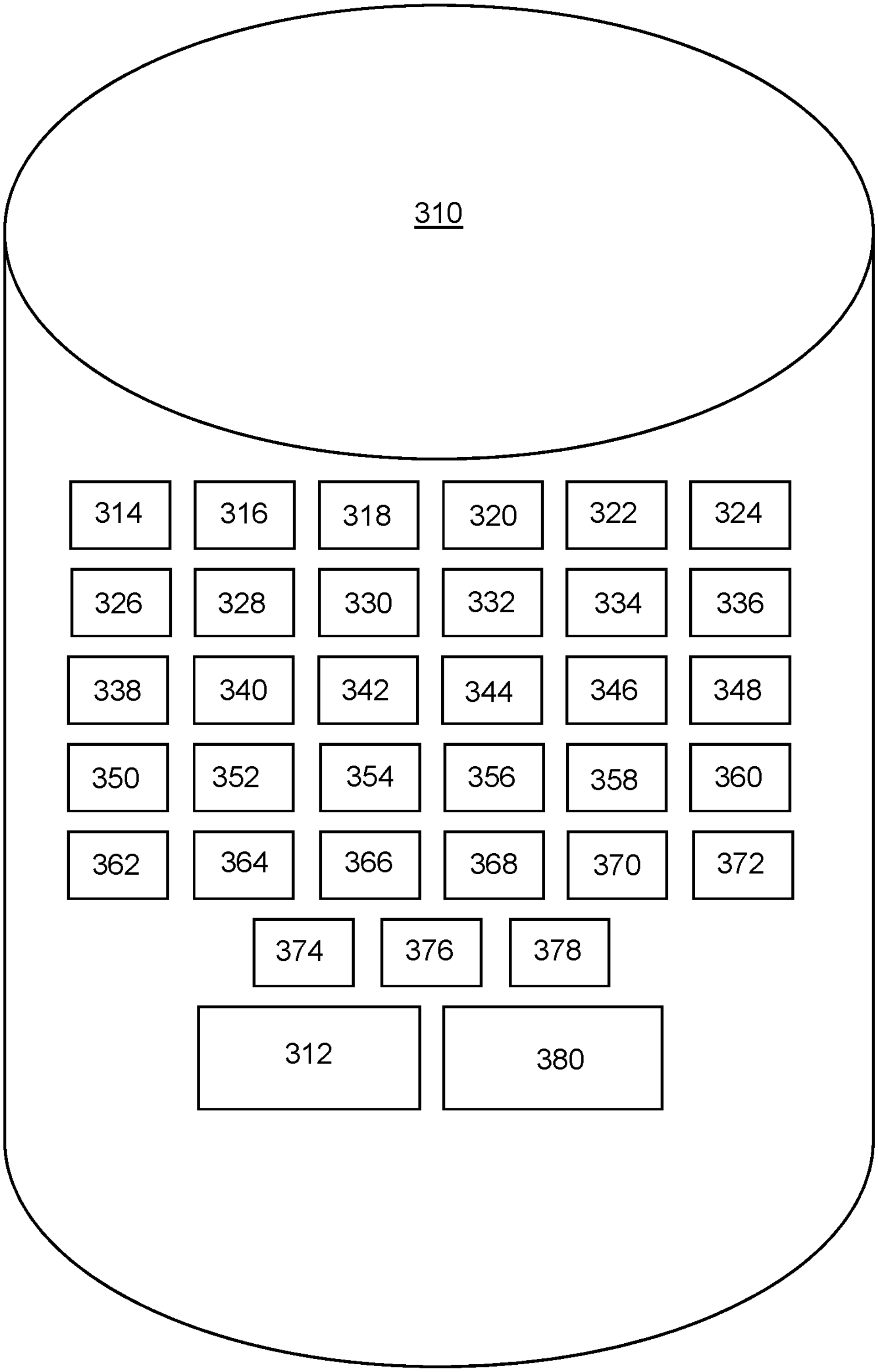
FIG. 3 is a diagram illustrating an example of a device memory according to an embodiment.

FIG. 3 is a diagram schematically illustrating an example of a memory 310 according to an embodiment. The memory 310 may be configured to store, for example, program instructions 312. The memory may also be configured to store various information detected, determined or received by the ostomy leak detection system such as the ostomy system information and/or characteristic information. For example, the stored information may include, but is not limited to, sensor information 314, parameter information 316, product consumption information 318, use information 320, inventory information 322, SKU information 324, quantity information 326, additional information 328, leak information 330, gas information 332, diet information 334, stoma health information 336, images or image information 338, troubleshooting information 340, diagnostic information 342, wear time information 344, aggregated information 346, user country and/or location information 348, ostomy type information 350, product type information 352, user age information 354, climate information 356, user activity information 358, product age information 360, product manufacture information 362, product source information 364, predictive information 368, environmental information 370, stoma type information 372, stoma output information 374, body type information 376, recommendation information 378, training model(s) 380 and the like. The memory 310 may comprise a plurality of memory devices at different auxiliary devices. Each of the memory devices may be configured to store some or all of the information of the present embodiments. Memory devices of different auxiliary devices may store different information from one another as well.

Figure 4:
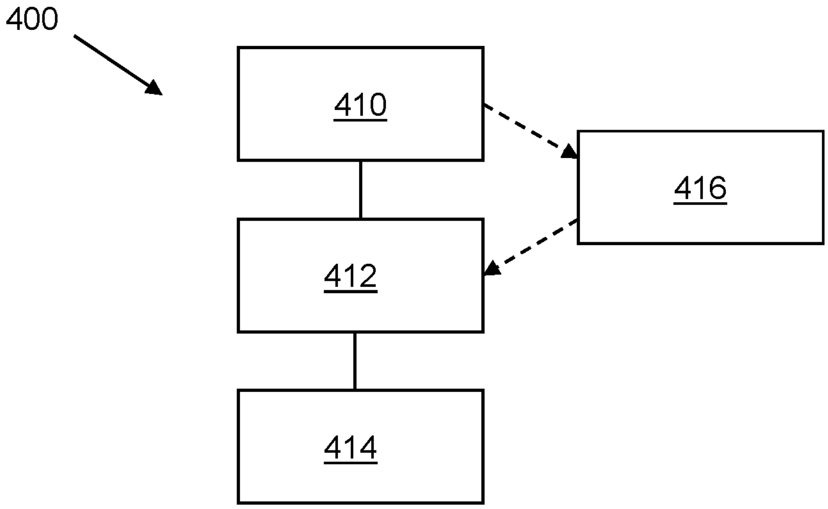
FIG. 4 is a block diagram illustrating an example of a method for ostomy leak detection analysis according to an embodiment.

FIG. 4 is a block diagram illustrating a method 400 for ostomy leak detection system analysis according to an embodiment. At 410, the method may include receiving ostomy system information relating an ostomy product. The ostomy system information may be received, for example, via a sensor device (e.g., detected information), user input, and/or from an auxiliary device including information stored by an auxiliary device or determined by an auxiliary device. The ostomy system information may include, for example, any information described in embodiments herein and/or any other relevant information relating to factors which may affect performance of an ostomy product. In an embodiment, the ostomy system information may be received by an auxiliary device.

At 412, the method may include determining characteristic information based on the ostomy system information. Characteristic information may include, for example, product consumption information, leak information, inventory information, stoma health information, replacement or time to replace information, recommendation information, predictive information and the like. One or more of the auxiliary devices may determine the characteristic information.

At 414, the method may optionally include providing a notification. The notification may be provided based on, for example, the determined characteristic information. The notification may be provided by one or more of the auxiliary devices.

At 416, the method may optionally include aggregating ostomy system information from a plurality of ostomy leak detection systems corresponding to a plurality of different users and/or ostomy products. Characteristic information may be determined based on the aggregated ostomy system information. One or more of the auxiliary devices may be configured to aggregate the ostomy system information. In an embodiment, the characteristic information may be aggregated as well, for example, by one or more of the auxiliary devices. For example, in an embodiment, a server device may aggregate ostomy system information and/or characteristic information.

It will be appreciated that numerous factors not specifically described above may affect performance of an ostomy product, such as an ostomy accessory, an ostomy appliance and/or an ostomy pouch. Such factors may be specific to the user, the ostomy product, the environment, and/or the manufacturer, for example. Information relating to such factors, such as the ostomy system information, may be provided to an ostomy leak detection system and used as a basis for determining (including predicting) one or more characteristics of the ostomy product. The factors affecting performance of an ostomy product and the one or more characteristics of the ostomy product may further be used by ostomy specialists, clinicians, users and other relevant personnel for managing ostomy care for the patient/user.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy leak detection system comprising:

a sensor device configured to detect one or more parameters or parameter values indicative of a condition of an ostomy product; and one or more auxiliary devices operably connected to the sensor device and configured to receive sensor information indicative of the condition of the ostomy product from the sensor device, wherein the one or more auxiliary devices includes at least one of monitoring device, a wearable device, a consumer electronic device and a server device, wherein the sensor device is configured to sync with the one or more auxiliary devices each time the ostomy product is replaced, and wherein the one or more auxiliary devices is configured to develop ostomy product consumption information in accordance with a count of syncing operations between the sensor device and the one or more auxiliary devices.

2. The ostomy leak detection system of claim 1, wherein one or more of the auxiliary devices is configured to determine and/or receive ostomy system information.

3. The ostomy leak detection system of claim 2, wherein one or more of the auxiliary devices is configured to determine characteristic information of an ostomy product based at least in part on the ostomy system information.

4. The ostomy leak detection system of claim 3, wherein one or more of the auxiliary devices is configured to aggregate and store the ostomy system information and/or the characteristic information from a plurality of users and/or ostomy products.

5. The ostomy leak detection system of claim 1, wherein the sensor device is a leakage sensor device configured to detect electrical resistance.

6. The ostomy leak detection system of claim 1, wherein the one or more auxiliary devices includes the wearable device operably connected to the sensor device and a consumer electronic device communicably connected to the wearable device via a wireless connection.

7. The ostomy leak detection system of claim 1, wherein the one or more auxiliary devices includes a monitoring device operably coupled to the sensor device, a wearable device communicably coupled to the monitoring device, and a consumer electronic device communicably connected to the wearable device via a wireless connection.

8. The ostomy leak detection system of claim 1, wherein the at least one auxiliary device includes a server device communicably coupled to one or more of the wearable device and the consumer electronic device.

9. The ostomy leak detection system of claim 1, further comprising an ostomy product, wherein the sensor device is operably connected to the ostomy product.

10. The ostomy leak detection system of claim 1, wherein the one or more auxiliary devices comprises a server device and the server device aggregates sensor information from a plurality of ostomy leak detections systems corresponding to a plurality of different users to develop aggregated data.

11. The ostomy leak detection system of claim 10, wherein the server device is configured to determine predictive information based on the aggregated data, wherein the predictive information includes an approximation of when an ostomy product may be expected to leak.

12. The ostomy leak detection system of claim 10, wherein the server device is configured to determine characteristic information from the aggregated data, wherein the characteristic information includes product consumption information, leak information, inventory information, replacement or time to replace information, and/or recommendation information.

* * * * *